(12) United States Patent
Scheremet et al.

(10) Patent No.: US 9,295,766 B2
(45) Date of Patent: *Mar. 29, 2016

(54) KIT FOR LOW PROFILE THORACIC WOUND SEAL WITH LATERALLY-DIRECTED DISCHARGE

(71) Applicant: FastTrack Medical Solutions LLC, Eden Prairie, MN (US)

(72) Inventors: William Scheremet, Hinckley, MN (US); Steven J. Brinkman, Minneapolis, MN (US); Kim Jacobsen, Minneapolis, MN (US)

(73) Assignee: FastTrack Medical Solutions LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,757

(22) Filed: Dec. 20, 2013

(65) Prior Publication Data

US 2014/0207120 A1 Jul. 24, 2014
US 2015/0119864 A9 Apr. 30, 2015

Related U.S. Application Data

(63) Continuation of application No. 13/647,369, filed on Oct. 8, 2012, now Pat. No. 8,637,725, which is a continuation-in-part of application No. 12/857,522, filed on Aug. 16, 2010, now Pat. No. 8,309,786.

(60) Provisional application No. 61/544,362, filed on Oct. 7, 2011.

(51) Int. Cl.
*A61F 13/00* (2006.01)
*A61M 1/04* (2006.01)
*A61F 13/14* (2006.01)

(52) U.S. Cl.
CPC ............... *A61M 1/04* (2013.01); *A61F 13/143* (2013.01)

(58) Field of Classification Search
CPC ............................. A61F 13/143; A61M 1/04
USPC ....................................................... 602/41–54
See application file for complete search history.

(56) References Cited

U.S. PATENT DOCUMENTS 3,954,105 A 5/1976 Nordby et al.
4,465,062 A 8/1984 Versaggi et al.
(Continued)

FOREIGN PATENT DOCUMENTS

AU 1587692 A1 10/1992
CA 2104966 8/1992
(Continued)

OTHER PUBLICATIONS

International Search Report and Written Opinion in PCT/US2011/47702 May 10, 2013, 3 pages.

*Primary Examiner* — Michael Brown
(74) *Attorney, Agent, or Firm* — Craige Thompson; Thompson Patent Law

(57) ABSTRACT

Apparatus and associated methods for a wound valve assembly provide an annular space extending radially around a central portion of a valve, which valve acts to substantially relieve pressure build up in a thoracic cavity when applied to a thoracic wound. In an illustrative example, the valve assembly may form an annular space that extends radially in all directions around a check valve. In some examples, gasses and exudates may flow substantially radially and/or parallel to the patient's local body. Various embodiments may advantageously provide open fluid communication for the gasses and exudates escaping from the wound when the valve assembly is partially covered (e.g., body armor, clothing, blankets), or when the patient may be lying down on the side of the body with the wound, for example.

9 Claims, 18 Drawing Sheets

(56) References Cited

U.S. PATENT DOCUMENTS

| | | |
|---|---|---|
| 4,717,382 A | 1/1988 | Clemens et al. |
| 5,160,322 A | 11/1992 | Scheremet et al. |
| 5,431,633 A | 7/1995 | Fury |
| 5,478,333 A | 12/1995 | Asherman, Jr. |
| 5,520,632 A | 5/1996 | Leveen et al. |
| 7,504,549 B2 | 3/2009 | Castellani et al. |
| 7,615,674 B2 | 11/2009 | Asherman |
| 8,309,786 B2 * | 11/2012 | Scheremet et al. ............ 602/43 |
| 8,637,725 B2 * | 1/2014 | Scheremet et al. ............ 602/43 |
| 2007/0232978 A1 | 10/2007 | Castellani |
| 2008/0033377 A1 | 2/2008 | Kauth et al. |
| 2008/0091152 A1 | 4/2008 | Asherman |
| 2008/0178884 A1 | 7/2008 | Gerson et al. |
| 2008/0234726 A1 | 9/2008 | Biddle et al. |

FOREIGN PATENT DOCUMENTS

| | | |
|---|---|---|
| EP | 0596889 | 5/1994 |
| WO | WO9215344 | 9/1992 |

* cited by examiner

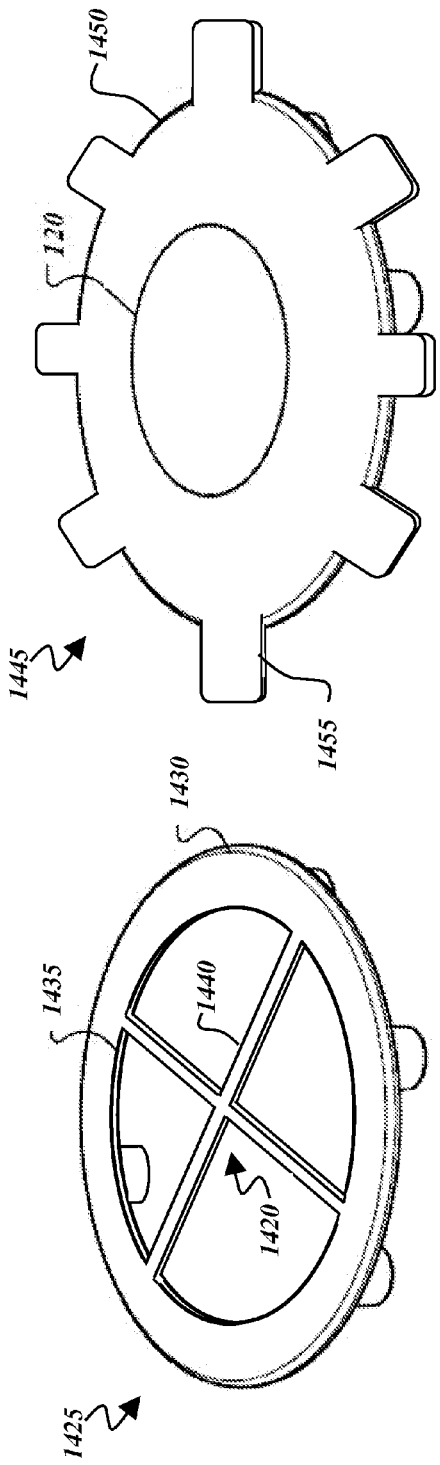
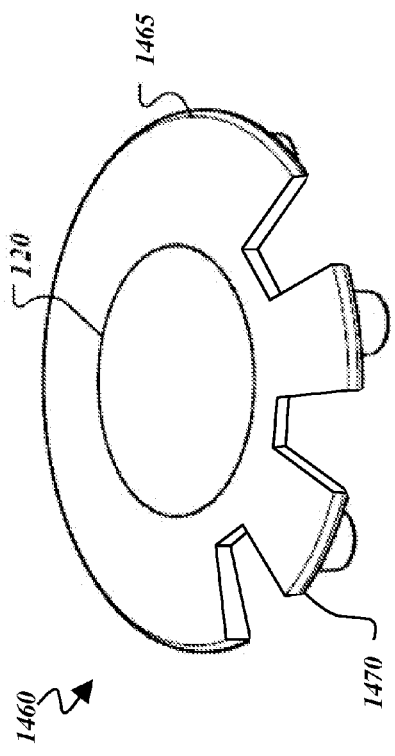
FIG. 14B
FIG. 14C
FIG. 14D

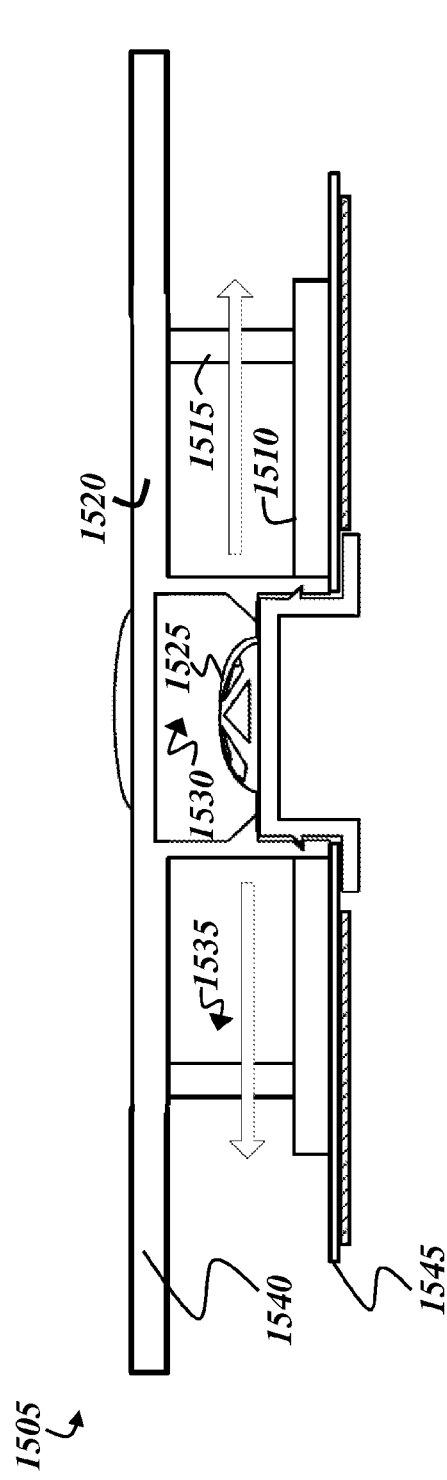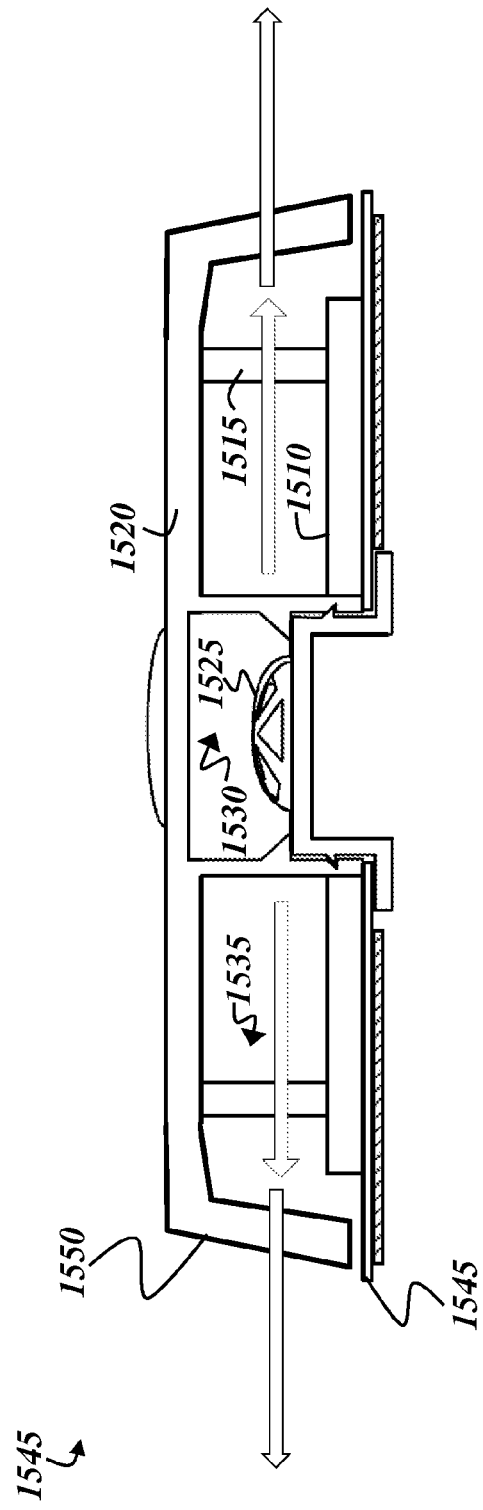
FIG. 15A
FIG. 15B

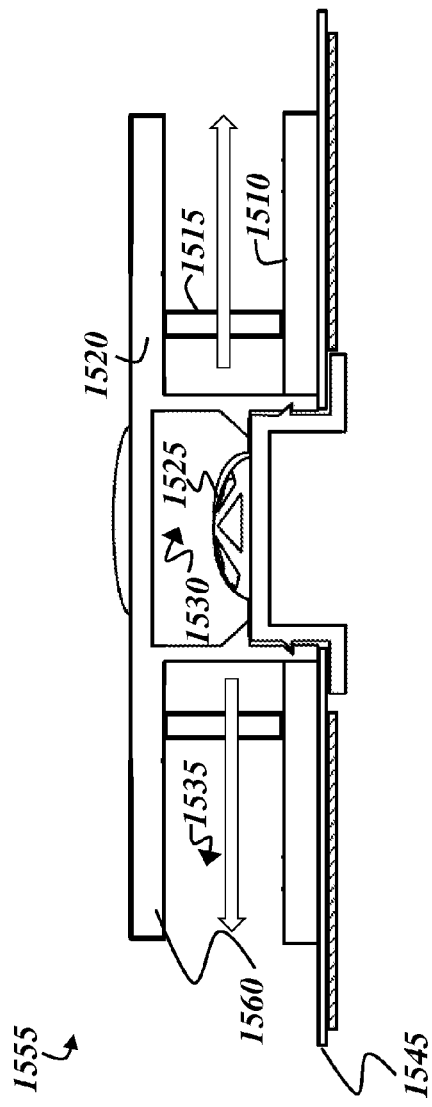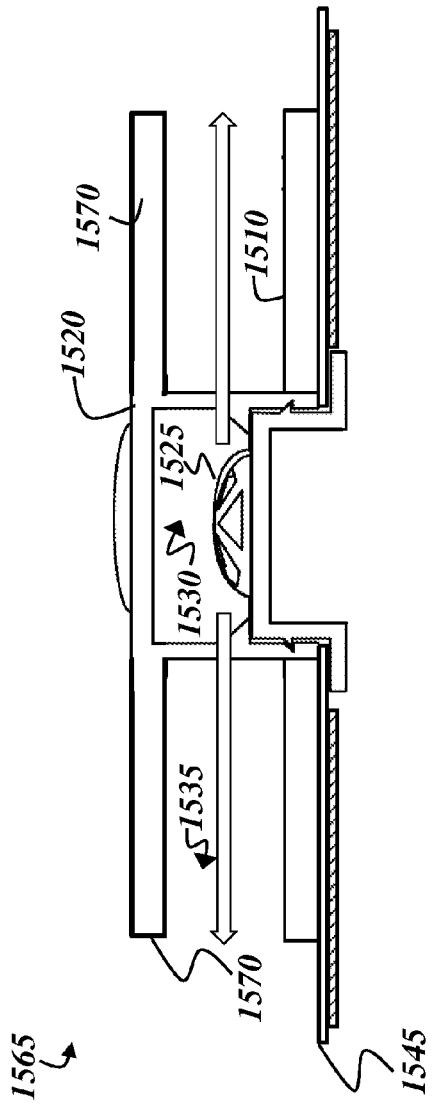

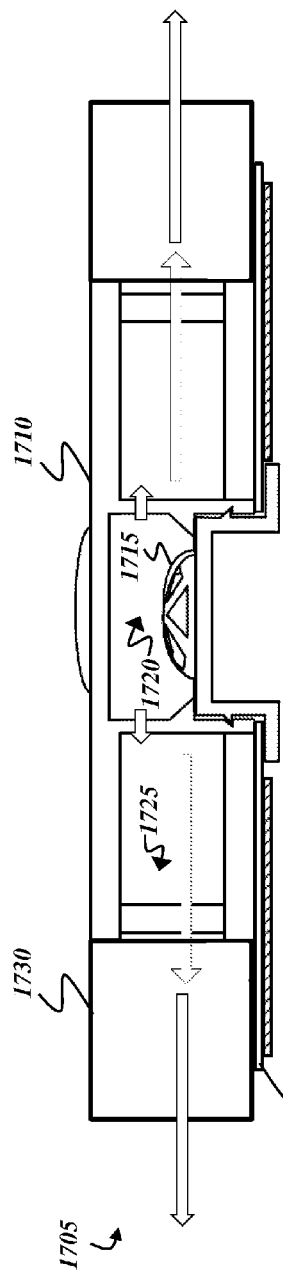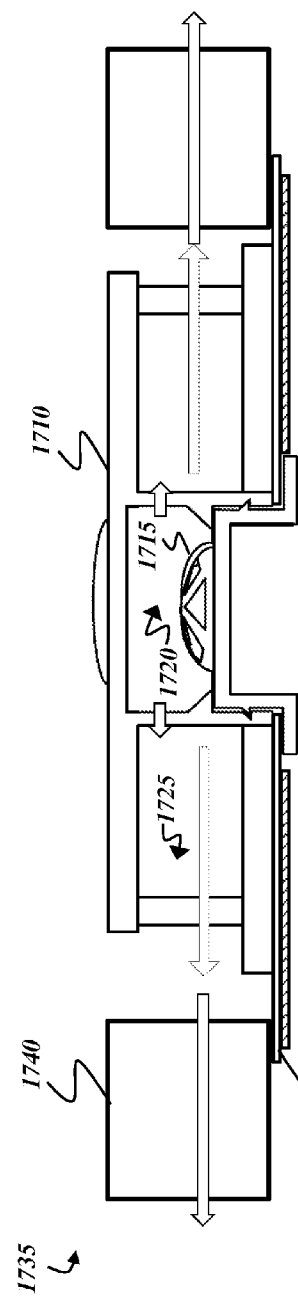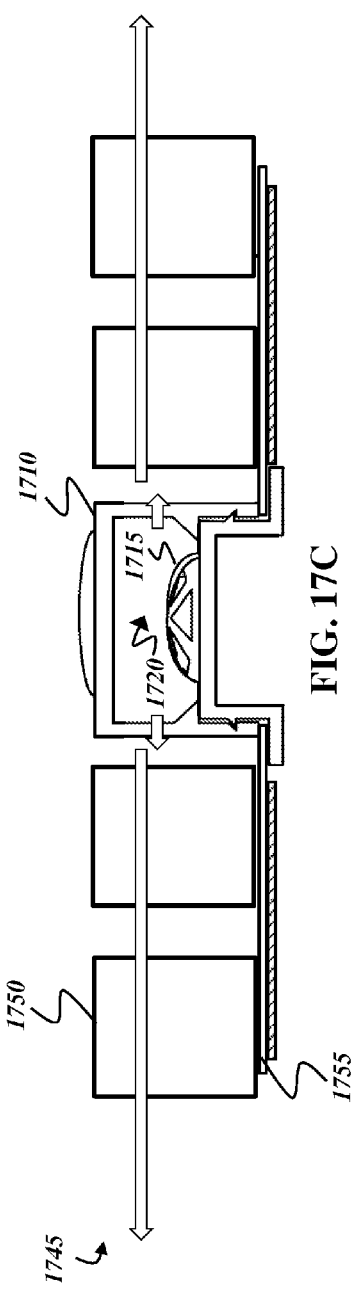

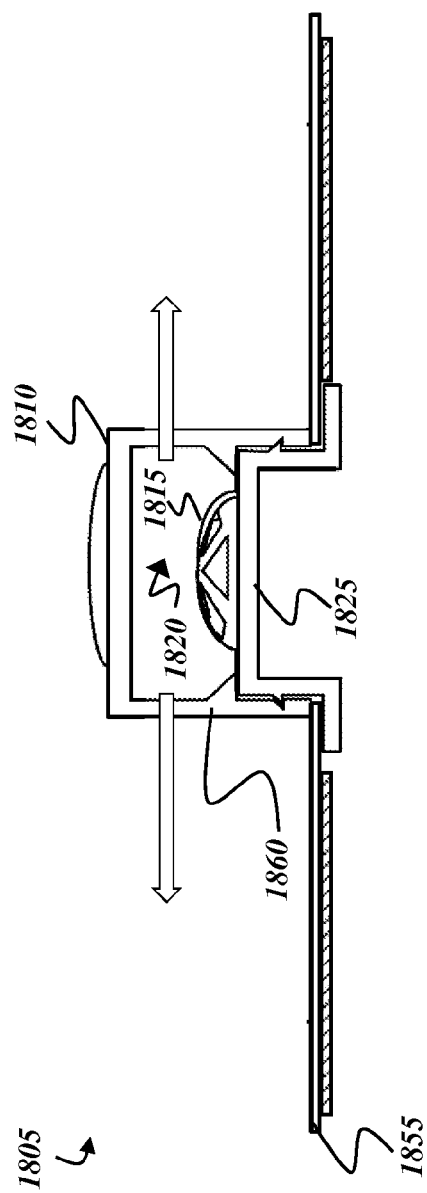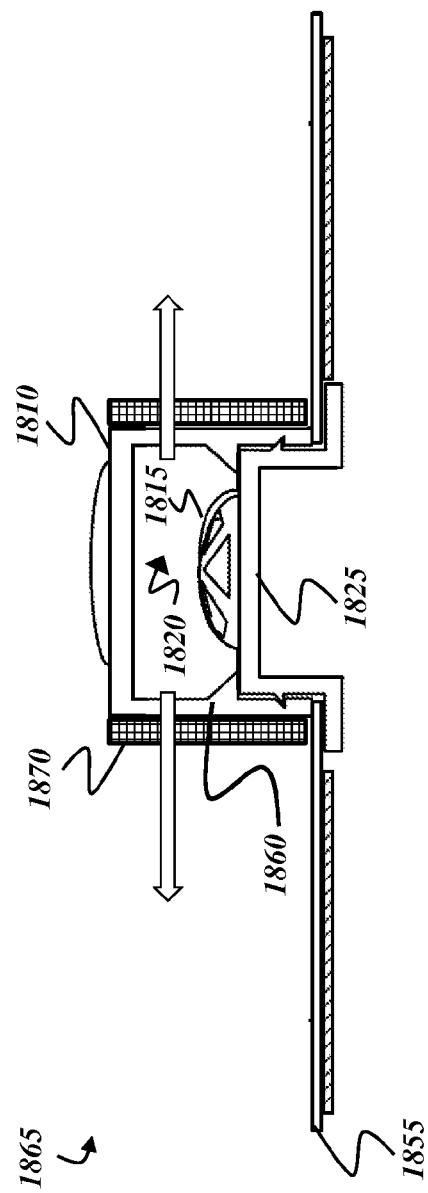

KIT FOR LOW PROFILE THORACIC WOUND SEAL WITH LATERALLY-DIRECTED DISCHARGE

CROSS-REFERENCE TO RELATED APPLICATIONS

The instant application is related to and claims priority to the following United States patent applications, the entirety of each of which is incorporated herein by reference.

| Ser. No. | Title | Filing Date |
| --- | --- | --- |
| 13/647,369 | Kit for Low Profile Thoracic Wound Seal with Laterally-Directed Discharge | Oct. 8, 2012 |
| 12/857,522 | Low Profile Thoracic Wound Seal with Laterally-Directed Discharge | Aug. 16, 2010 |
| 61/544,362 | Hydrogel Wound Covering Membrance Having Antimicrobial and Adhesive Properties | Oct. 7, 2011 |

TECHNICAL FIELD

Various embodiments relate generally to apparatus or methods for sealing thoracic wounds while relieving pressure build-up in a thoracic cavity.

BACKGROUND

In the event of a serious injury, it often falls to the first responders to quickly stabilize a patient for transport to an appropriately equipped medical care facility. The first responders are often trained to assess patients' injuries. They may often be required to determine appropriate procedures to quickly stabilize a traumatic injury, and to determine what their limitations may be in terms of time to treat before transport in view of the criticality of the patient's wounds.

One type of serious injury that may be encountered as a result of, for example, a military encounter, is a bullet or knife wound. In the event of a gunshot or knife wound penetrating the chest or thoracic region, for example, a first responder may be equipped to apply a dressing over the wound. Punctures that penetrate the thoracic wall, however, are serious and demand immediate medical attention. Without access to a well equipped medical facility, there is a danger that a patient can develop a life-threatening condition, such as pneumothorax, if pressure is allowed to build up in the pleural space through the wound.

SUMMARY

Apparatus and associated methods for a wound valve assembly provide an annular space extending radially around a central portion of a valve, which valve acts to substantially relieve pressure build up in a thoracic cavity when applied to a thoracic wound. In an illustrative example, the valve assembly may form an annular space that extends radially in all directions around a check valve. In some examples, gasses and exudates may flow substantially radially and/or parallel to the patient's local body. Various embodiments may advantageously provide open fluid communication for the gasses and exudates escaping from the wound when the valve assembly is partially covered (e.g., by body armor, clothing, blankets), or when the patient may be lying down on the side of the body with the wound, for example.

Various embodiments may achieve one or more advantages. For example, some embodiments may provide an annular volume which may be maintained to provide fluid communication to discharge fluid pressure build up in the presence of clothing, blankets, body armor, or when laying on the side of the wound dressing assembly. Some embodiments of the valve may provide optical magnification to more easily inspect a check valve and to verify proper valve operation. Some embodiments may include a color-tinted valve membrane (e.g., yellow) which may substantially contrast with typical exudates (e.g., including blood) to further simplify the inspection and verification of valve operation. Various embodiments may include interference fit mechanisms for assembling the valve subcomponents to a soft pliable carrier (e.g., dressing bandage) to form a wound seal system. The carrier may provide a pliable, soft substrate for an aggressive hydrogel combined with an antimicrobial, whereby the combined assembly does not readily form channels that could break a seal of the valve against the patient, thereby providing an undesirable flow communication for allowing pressure build up in the pleural cavity, for example. As a further example, some embodiments may incorporate a hydrogel combined with an antimicrobial to releasably adhere the valve assembly to the patient, and to permit the immediate and direct application of the valve assembly to protect against pressure build up from an open thoracic wound in the field, for example.

The details of various embodiments are set forth in the accompanying drawings and the description below. Other features and advantages will be apparent from the description and drawings, and from the claims.

BRIEF DESCRIPTION OF THE DRAWINGS

FIGS. 14A-D depict exploded views of exemplary valve assemblies.

FIG. 15A-D depict cross sectional views of exemplary valve assemblies, such as those embodiments described with reference to FIGS. 14A-B.

FIGS. 17A-C depict cross sectional views of the exemplary thoracic wound seal assemblies of FIG. 16A-D.

FIGS. 18A-B depict cross sectional views of exemplary thoracic wound seal assemblies.

Like reference symbols in the various drawings indicate like elements.

DETAILED DESCRIPTION OF ILLUSTRATIVE EMBODIMENTS

FIGS. 1A-1D depict perspective, cross-sectional, plan, and elevation views of an exemplary valve assembly. In the depicted FIG. 1A, a low profile valve assembly 100 is positionable over a wound to limit pressure build-up in the thoracic cavity, for example. As will be described, the valve assembly 100 is configured for assembly to a soft, pliable carrier (not shown) that forms a substantially air-tight seal to the skin around the wound by virtue of an adhesive coating (e.g., hydrogel) on one surface of the carrier substrate (examples of which are described in further detail with reference to FIGS. 3 and 7). For purposes of clearly introducing embodiments of the valve assembly 100, the valve assembly 100 is shown without a carrier layer in FIGS. 1-2.

Figure 1A:
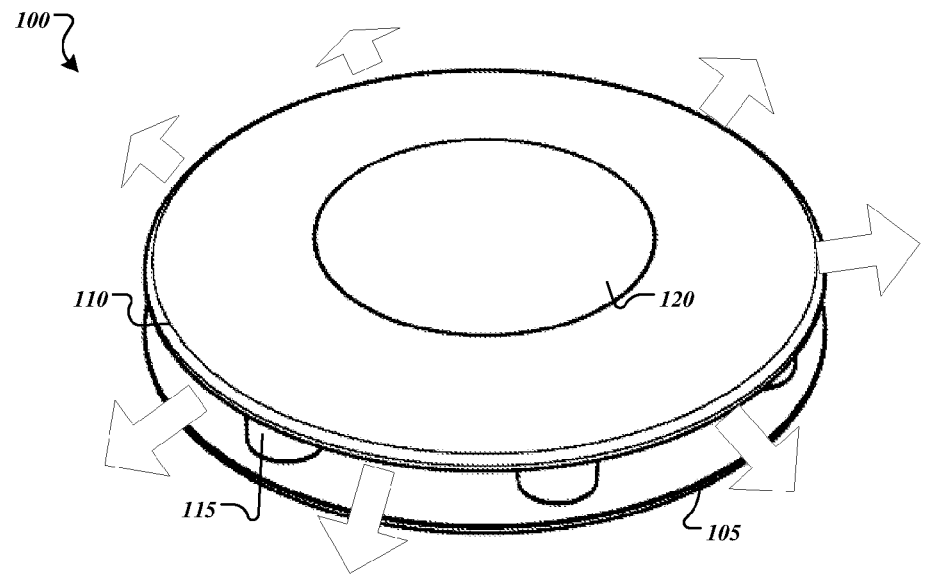
FIGS. 1A-1D depict perspective, cross-sectional, plan, and elevation views of an exemplary valve assembly.

In particular examples, the valve assembly 100 may provide for radial discharge of gasses (e.g., air) and/or exudates (e.g., blood) that may flow out of a thoracic wound. The arrows in the FIG. 1A depict lateral flow paths for communicating fluids (e.g., blood, gasses, or other exudates) radially away from the wound. The various flow paths permit lateral fluid flow in a plane substantially parallel to a plane tangent to the patient's body at the wound site. In some examples, substantially lateral and radial flow paths may substantially reduce the risk that all the flow paths will be occluded by materials (e.g., such as clothing, blankets, body armor) or when the patient is lying on the side of the body with the valve assembly 100. In an illustrative example, a patient may be treated with two valve assemblies 100, one on a front entry thoracic wound and one on a rear exit thoracic wound, and the patient may need to lie down on the back during transport, for example.

The valve assembly 100 includes a bottom housing 105 and a top housing 110. The housings 105, 100 each include an annular flange lying in substantially parallel planes. Between the facing surfaces of the respective annular flanges are a number of support bosses 115. The support bosses 115 are disposed in a volume between the annular flanges of the housing 105, 110 that form an annular cavity to permit lateral fluid flow discharge from the valve assembly 100 (see exemplary arrows).

In this embodiment, the top housing 110 further includes an optical gain element, a lens 120, configured to magnify a view of an interior operation of the valve assembly. In particular examples, the lens may enhance an image of the valve operation, to permit an attending care provider, to monitor operation of a unidirectional valve, for example. Operations of exemplary valves will be described in further detail, for example, with reference to FIGS. 2-6.

Figure 1B:
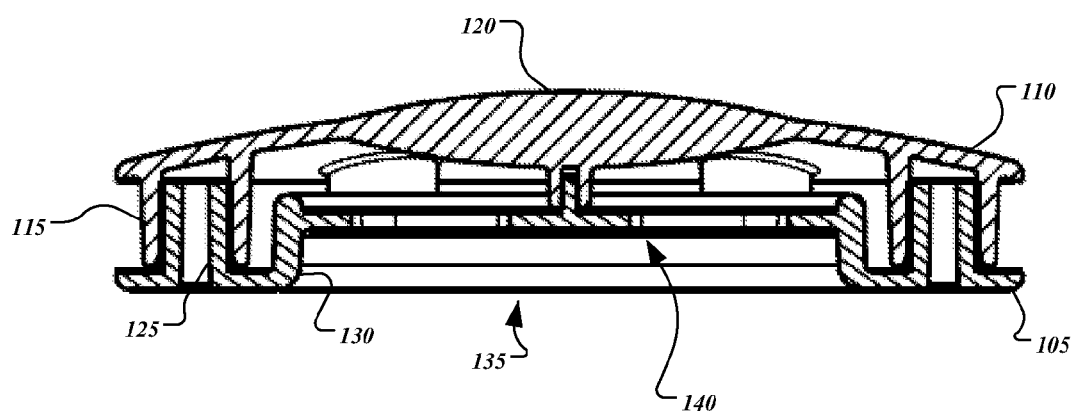
Figure 1C:
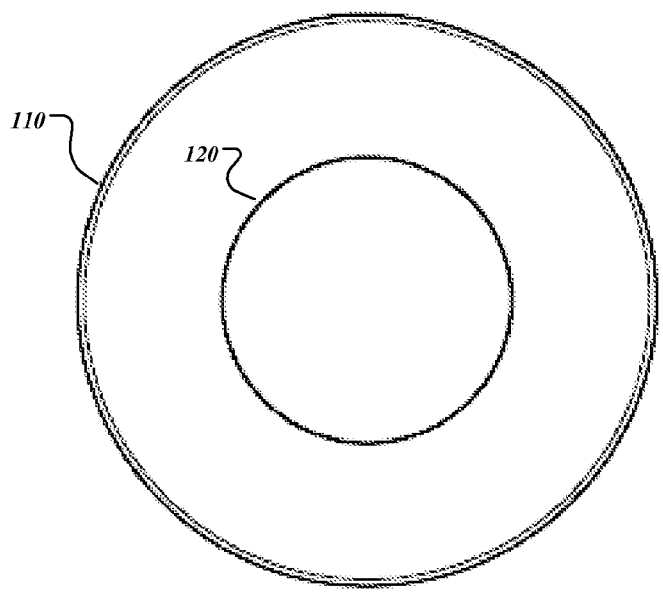
Figure 1D:
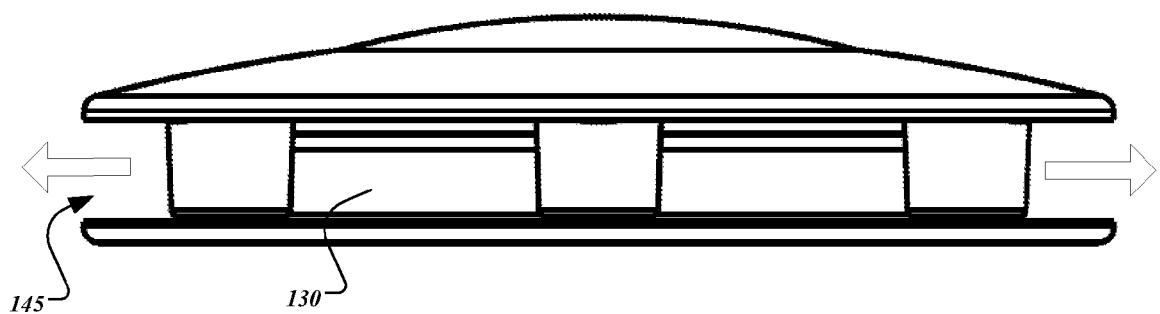

FIG. 1B-1D show cross-section, top, and plan views that reveals further detail of the exemplary valve assembly 100 of FIG. 1A. The bottom housing 105 further includes support pins 125 that correspond to the support bosses 115. When registered in alignment and assembled, each of the support pins 125 provide an interference fit to engage an interior of a corresponding one of the support bosses 115. The coupling of the support pins 125 to the support bosses 115 further engage a carrier (not shown in this figure). The support pins 125, being covered by the carrier, drive a local portion of the carrier material web into the support bosses 115, thereby securely engaging the carrier to the assembled bottom and top housings 105, 110.

The bottom housing 105 further includes a central frame 130, which defines a bottom aperture 135 through which fluids pass through a valve system 140 and then discharge laterally through an annular cavity 145 (see FIG. 1D).

In the depicted example, a bottom portion of the lens 120 includes a boss to engage and couple to a projection of the valve system. This coupling may, in some embodiments, secure the valve membrane to the membrane mounting pin, as will be described in further detail with reference to FIGS. 2A-2B.

The lens 120 is depicted, as an example, with a variable thickness profile such that, according to the relative indices of refraction, an observer can view an image of the interior of the valve assembly with the benefit of a magnification factor. In some implementations, this may advantageously permit closer inspection of the small movements and small quantities of materials in the valve system 140. The lens 120 portion may be a substantially transparent plastic or glass material. In some examples, the lens 120 may be made of a substantially different material (e.g., glass, high density polyethylene) than the remainder of the top housing 110 (e.g., polypropylene). In some embodiments, the lens 120 may be formed from materials arranged to provide a graded index of refraction (GRIN) to yield an optical gain or magnification.

Figure 2A:
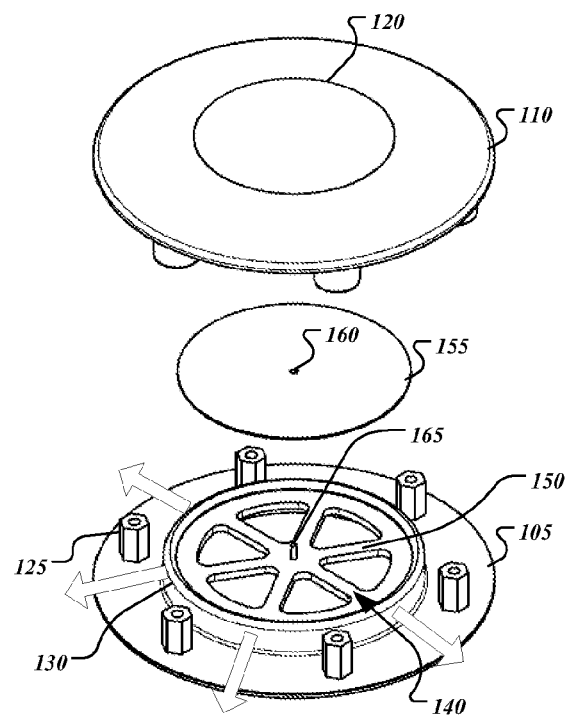
FIGS. 2A-2B depict exploded perspective views of the example of FIGS. 1A-1D.
Figure 2B:
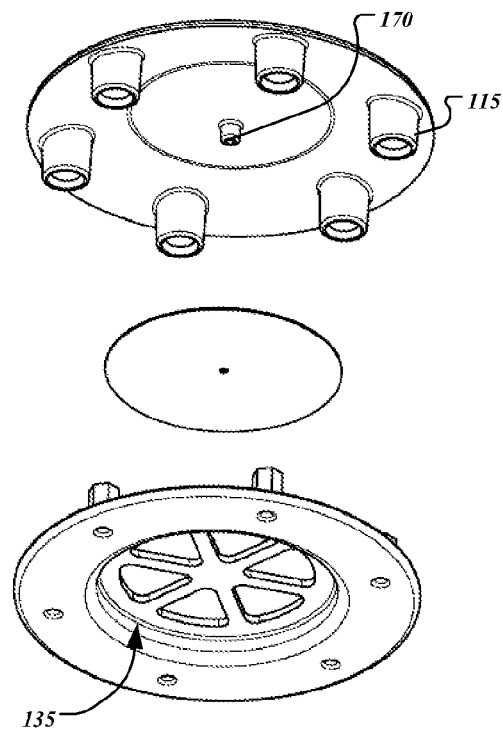

FIGS. 2A-2B depict exploded perspective views of the example of FIGS. 1A-1D. FIG. 2A shows an exemplary embodiment of an interior of the valve system 140. In particular, the central frame 130 further includes a membrane support member 150 arranged as a number of spokes formed between a peripheral ring and a central hub. In the depicted embodiment, a valve membrane 155 is sized to lie on the membrane support member 150 within the upward extending wall of the central frame 130. The central hub of the central frame 130 includes a mounting pin 165 to register and locate the mount aperture 160 of the valve membrane 155.

The bottom housing 105 and the top housing 110 may extend radially from a central axis along which the mounting pin 165 is aligned. In some embodiments, a ratio of a radius to the periphery of the annular cavity 145 to a radius of an outer diameter of the central frame 130 may be about 1.25, 1.5, 1.75, 2.0, 2.25, 2.5, 2.75, 3.0, 3.25, 3.5, 3.75, 4.0, 4.25, 4.5, or at least about 5.0.

Figure 4:
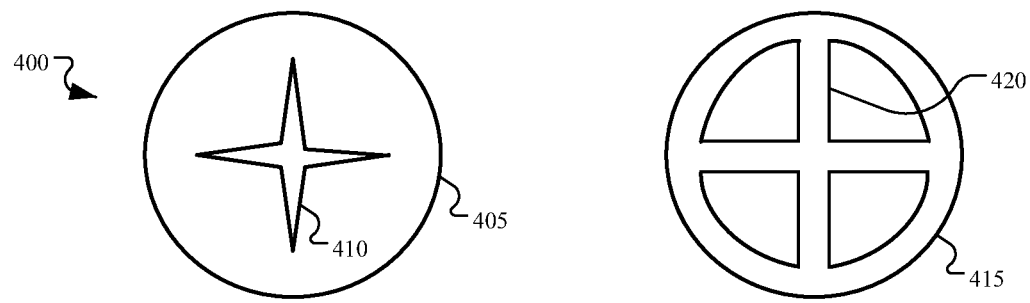
FIGS. 4-6 depict sets of exemplary valve membranes and corresponding membrane platforms.

Another exemplary embodiment of the valve system 140 is described, for example, with reference at least to FIG. 4 of U.S. Pat. No. 5,160,322 to Scheremet, et al., entitled "Occlusive Chest Sealing Valve," as issued Nov. 3, 1992.

In the depicted example, the valve membrane 155 rests on the membrane support member 150 and lies substantially in a plane. In some other embodiments, the support member 150 may be formed as a curved (e.g., concave, convex) surface.

Figure 3A:
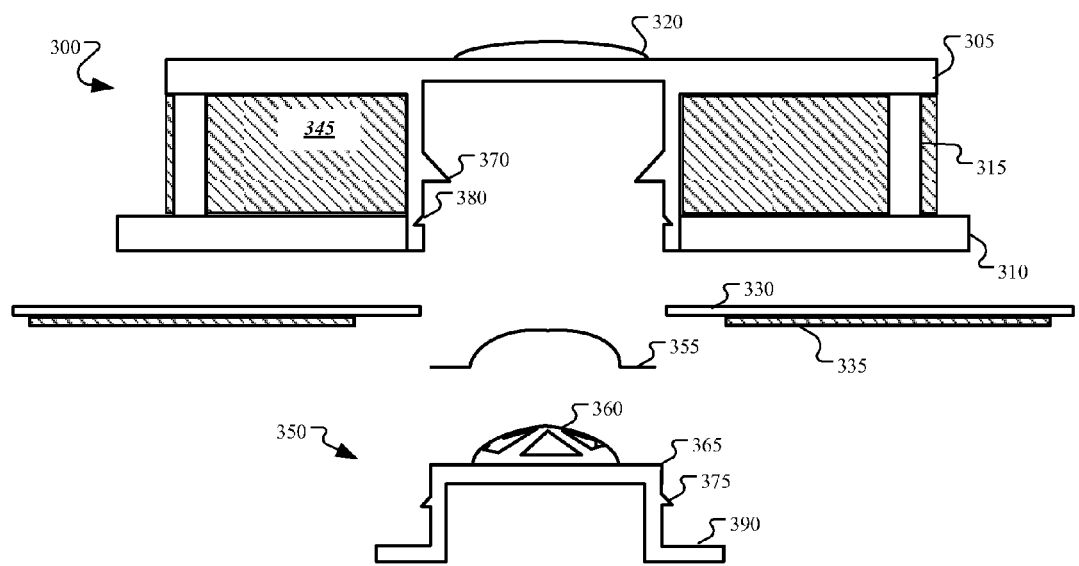
FIGS. 3A-3B depict cross-sectional exploded and assembled side views of an exemplary thoracic wound seal assembly.
Figure 3B:
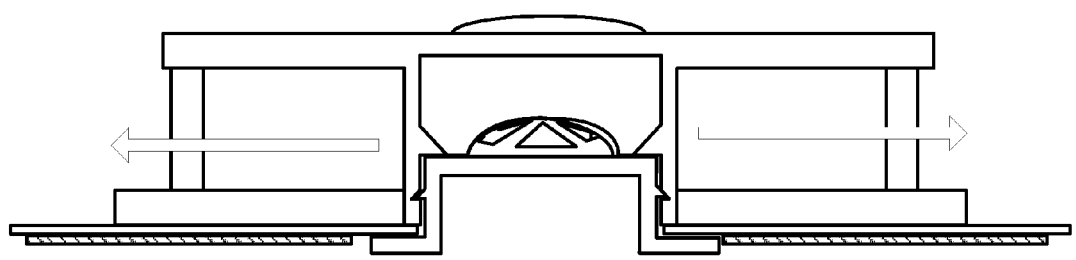

FIGS. 3A-3B depict cross-sectional exploded and assembled side views of an exemplary thoracic wound seal assembly. This embodiment depicts an exemplary valve support member having a curved surface.

FIG. 3A shows an exemplary wound seal assembly 300 that includes a base 305, a carrier 330, and a valve assembly 350. When assembled, as shown in FIG. 3B, these components form an embodiment of a thoracic wound seal.

The base 305 includes a base flange 310, supports 315, and a lens 320. The supports 315 form an annular cavity 345 in the space between the base flange 310 and an upper portion of the base 305, outside of a central portion configured to receive the valve assembly 350.

The carrier 330 is formed of a soft, pliable material that can provide a substrate for an adhesive layer 335 on one surface. In various embodiments, the adhesive 335 may be selectively applied to the carrier 330, for example, outside of the portion that makes contact with the valve assembly 350. In various implementations, the adhesive 335 may include a hydrogel to provide a substantially air tight seal to the patient's skin.

In various embodiments the carrier 330 may be sufficiently soft and pliable to resist forming air channels when the patient's skin moves, or when initially applied to non-planar skin features. A sufficiently thick layer of hydrogel may advantageously conform substantially to the patient's body to allow the valve assembly 350 to maintain a substantial seal around the wound site.

In some embodiments, the hydrogel may include or be modified to include at least one anti-microbial agent to protect the patient against infection. In some examples, the anti-microbial agent may include a silver-containing compound (e.g., salt of silver).

The valve assembly 350 receives a valve membrane 355 disposed on a curved membrane support 360, which has apertures through which exudates and gasses may flow from the wound to the annular cavity 345. The membrane support 360 rests on a valve base 365, which has a cylindrical shape. On a perimeter of the valve base 365 is disposed a ring 375 and a valve flange 390.

In the base 305, the central portion to receive the valve assembly 350 includes, in this embodiment, a locating ring 370 to provide a vertical stop that locates the valve assembly 350 within the central portion. The central portion further includes a recess 380.

To assemble the wound seal assembly 300, as shown in FIG. 1B, the carrier 350 is captured between the base flange 310 and the valve flange 390. The valve membrane 355 is captured along its perimeter between the locating ring 370 and the valve base 365. The valve assembly 350 may be retained in position upon insertion when the ring 375 engages the corresponding recess 380. The valve assembly 350 may snap into place upon insertion such that a perimeter of the valve membrane 355 is held in compression.

The assembled wound seal assembly 300 permits unidirectional fluid flow from the wound, through the valve assembly 355. Fluids may then be discharged laterally through the annular cavity 345 in any radial direction out of the base 305.

Operation of the perimeter-capture membrane will next be further described with reference to the embodiments depicted in FIGS. 4-6.

Figure 5:
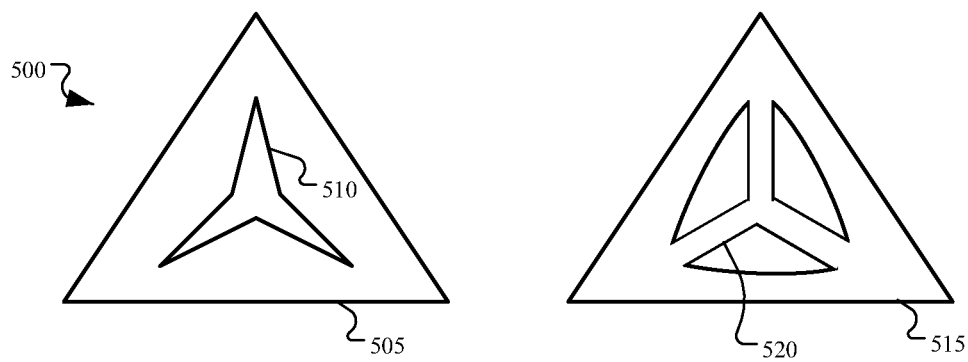
Figure 6:
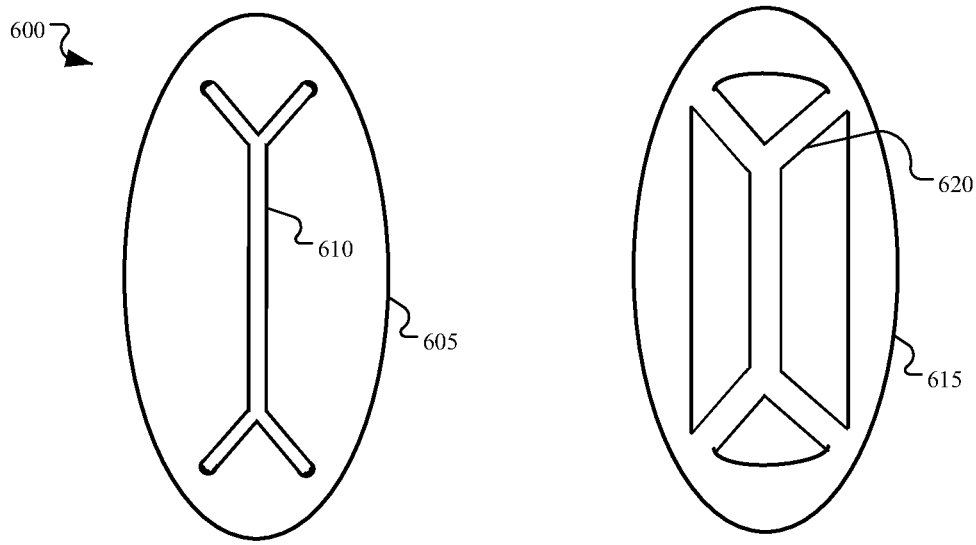

FIGS. 4-6 depict sets of exemplary valve membranes and corresponding membrane platforms. As shown in FIGS. 3A-3B, the perimeter of these valve membranes are captured and thus securely located. The embodiments of FIGS. 4-6 may be implemented in a planar (flat) support member (e.g., see membrane support member 150) or on a support member with a curved surface (e.g., see membrane support member 360). It is speculated by the inventors that a curved surface may be advantageous in yielding a reduced tendency for the membrane to become clogged, and there may be further advantages in sensitivity to releasing small pressures in the thoracic cavity, perhaps associated with the increased length of the aperture on a curved surface relative to a similar circumference valve in a planar format.

A valve embodiment 400 includes a membrane 405 with a single aperture 410. The aperture may be formed, for example, by cutting two crossed slits in a membrane. The membrane 405 is assembled on a valve base 415 so that the slits of the aperture 410 register along the corresponding membrane supports 420.

In operation, the valve responds to fluid pressure from the wound side (below the valve seal 415) by at least a portion of the membrane along the aperture 410 separating from the membrane support 420, permitting fluid to flow through the aperture. In response to fluid pressure from the atmospheric side, the valve assembly blocks reverse flow as the edges of the aperture 410 are in pressed in intimate contact with the membrane supports 420.

Similarly, FIGS. 5 and 6 depict exemplary valve embodiments 500, 600 in triangular and elliptical shapes, with membranes 505, 605 having apertures 510, 610, respectively. The membranes 505, 605 may be assembled on a valve base 515, 615 so that the slits of the aperture 510, 610 register along the corresponding membrane support structures 520, 620, respectively.

Figure 7A:
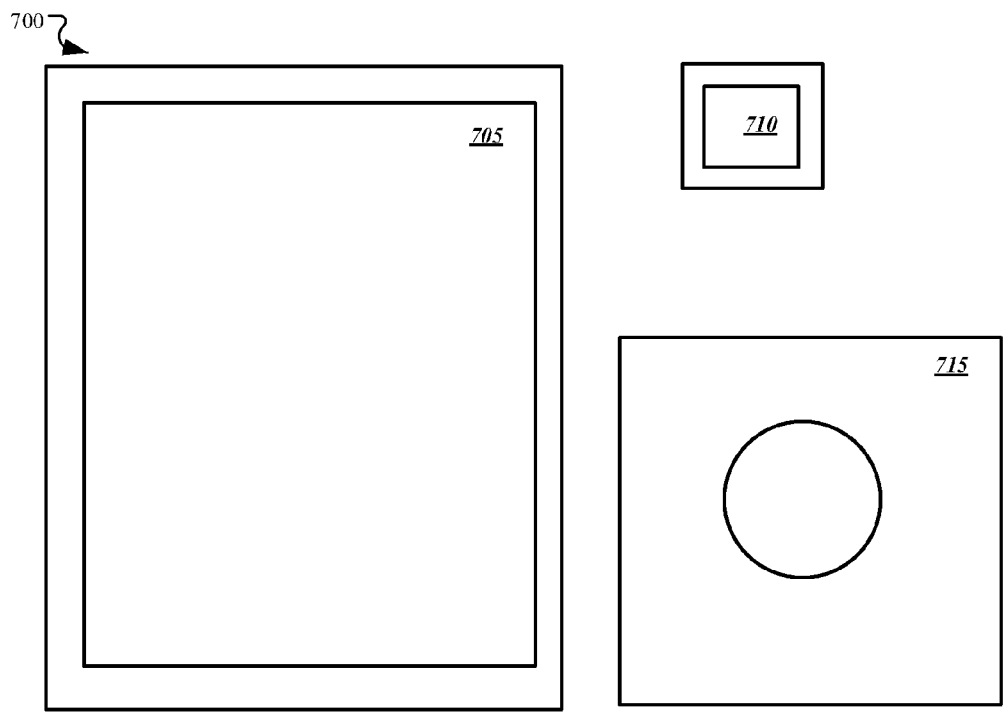
FIGS. 7A-7B depict plan views of exemplary kit for packaging an exemplary valve system.
Figure 7B:
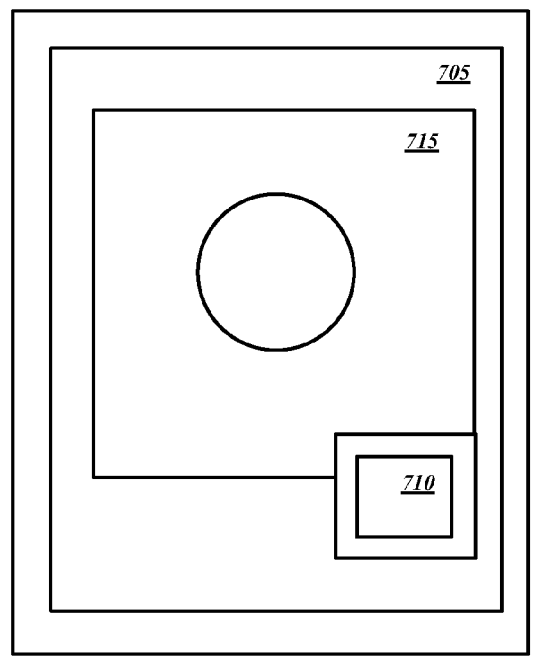

FIGS. 7A-7B depict plan views of an exemplary kit for packaging an exemplary valve system. It may be advantageous in some applications to have a kit 700 that includes a protective package 705, a pre-moistened anti-septic and/or anti-microbial wipe 710, and a thoracic wound seal 715. In some embodiments, the thoracic wound seal 715 may include a release liner to protect the hydrogel adhesive until ready for use. In some implementations, the packaging 705 may serve as a release liner directly, which may reduce the materials and/or manufacturing cost and further reduce the waste stream, for example.

In some implementations, the package 705 may have a foil backing on at least one or both sides. The package 705 may be vacuum sealed to substantially reduce or prevent ingress and/or egress of moisture or contaminants. A vacuum seal may advantageously extend the service life of the hydrogel, for example. In some examples, the kit may include a window on the package 705 to permit inspection of the contents. In some embodiments, the kit 700 may be rolled into a substantially cylindrical form for compact storage (e.g., in a medical bag).

Figure 8:
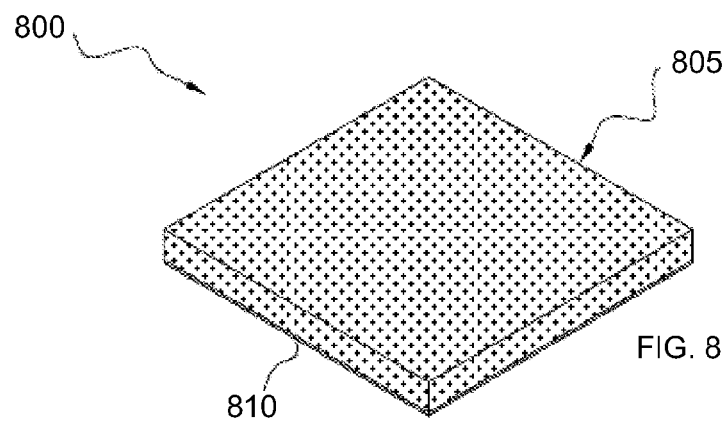
FIG. 8 depicts an upper perspective view of an exemplary membrane.

FIG. 8 depicts an upper perspective view of an exemplary membrane. The system 800 includes a membrane 805 and a release liner 810. The release liner 810 permits rapid separation when the membrane 805 is needed for use as a wound dressing, for example.

It should be appreciated that the term "membrane" is not meant to be limiting, and may in various implementations comprise a solid, semi-solid, or liquid composition, for example a pad, a patch, or a gel. The membrane 805 may be applied over the wound in one-piece, a patch or a conventional bandage, or the membrane 805 may be spread over the wound, for example, in a liquid or fluid-gel form. The membrane 805 may be formed into shapes of various sizes, for example, 6 inches×6 inches, 12 inches×12 inches, or 4 inches×18 inches.

Figure 9:
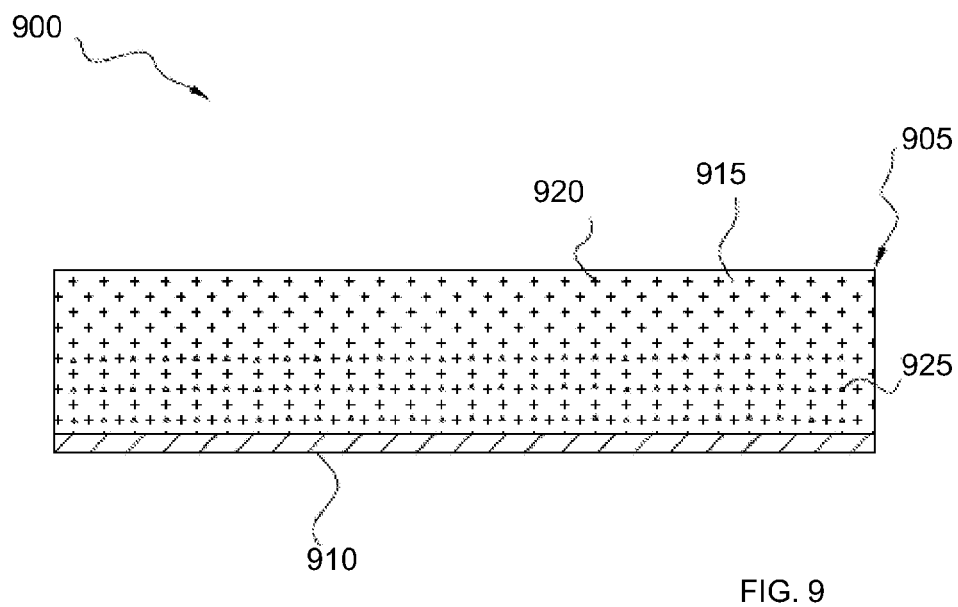
FIG. 9 depicts a cross-sectional view of the embodiment shown in FIG. 8.

FIG. 9 depicts a cross-sectional view of the embodiment shown in FIG. 8. The system 900 includes a membrane 905 includes a carrier substrate 915 comprised of a pliable material, for example, a hydrogel substance. As illustrated, the carrier substrate 915 may be rectangular in shape; however other shapes may be appreciated as will be discussed in reference to FIGS. 11-13.

The carrier substrate 915 includes an impregnated antimicrobial agent 920. The antimicrobial agent 920 may be evenly dispersed throughout the interior and/or exterior of the carrier substrate 915 or may be dispersed throughout only a portion of the carrier substrate 915, for example, along the bottom or contact surface of the carrier substrate 915.

The carrier substrate 915 includes an impregnated adhesive agent 925. The adhesive agent 925 may be evenly dispersed throughout the interior and/or exterior of the carrier substrate 915 or may be dispersed throughout only a portion of the carrier substrate 915, for example, along the bottom or contact surface of the carrier substrate 915. For example, if the adhesive agent 925 is dispersed only along a singular contact surface (e.g., bottom surface) of the carrier substrate 915 of the membrane 905, the non-contact surfaces (e.g., sides, top) of the carrier substrate 915 of the membrane 905 may include a barrier or composition such that would not contain the adhesive agent 925.

In another exemplary embodiment, an adhesive layer (not shown) may be formed or attached along the bottom or contact surface of the carrier substrate 915. Such an adhesive layer may still permit the antimicrobial agent 920 to make contact with the wound or fluids dispersed from the wound. An example of the adhesive layer may include tape, for example, 3M™ MEDIPORE™ TAPE, commercially available from 3M Corp. of Minnesota.

The adhesive agent 925 presents a tacky or sticky property such that the membrane 905 sticks to the supporting structure, for example, the skin of the patient, yet the adhesive agent 925 permits for easy removal of the membrane 905 from the supporting structure without causing a substantial disturbance or pulling on the supporting structure. For example, the disturbance may include the removal of hair, damage to the wound, tearing, or removal of a scab. The adhesive agent 925 also permits for the membrane to be attached to wet or dirty surfaces, thus not requiring the patient to clean the surface around the wound prior to attachment of the membrane 905.

Figure 10:
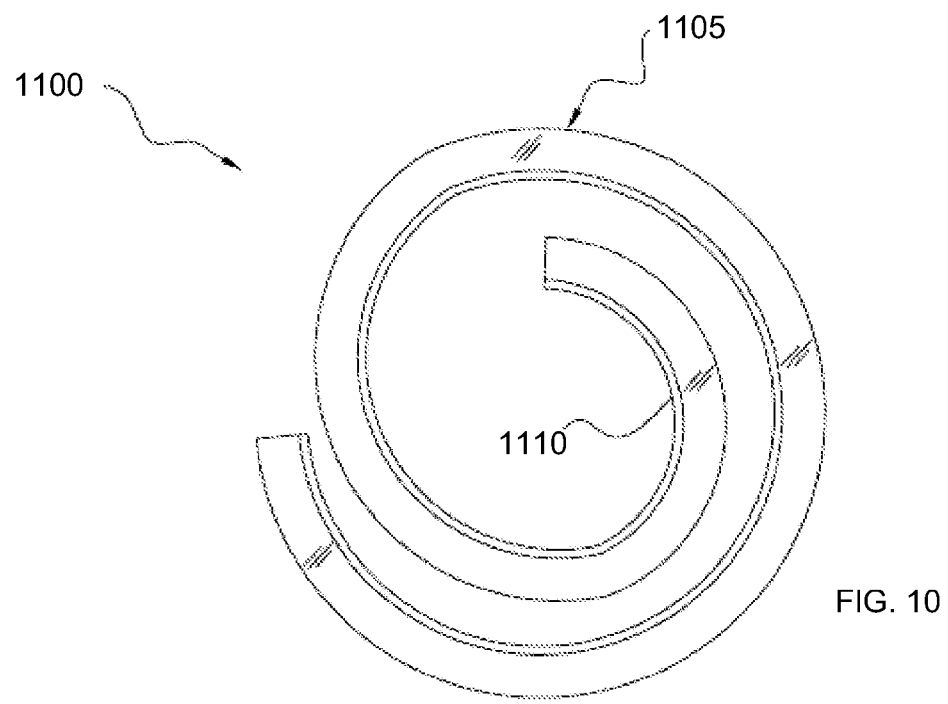
FIG. 10 depicts an exemplary side view of an embodiment illustrating the membrane being rolled.

FIG. 10 depicts an exemplary side view of an embodiment illustrating the membrane being rolled. Such an orientation of the system 1100 may advantageously permit convenient transport and storage of the system, such as in a medical bag or kit. FIG. 10 also illustrates the malleability of the system 1100, for example, the membrane 1105 being adapted for attachment to various shaped surfaces. Rolling in similar manner may be also employed for the kit 700, or various embodiments of a thoracic wound seal, such as the thoracic wound seal 715, for example.

Figure 11:
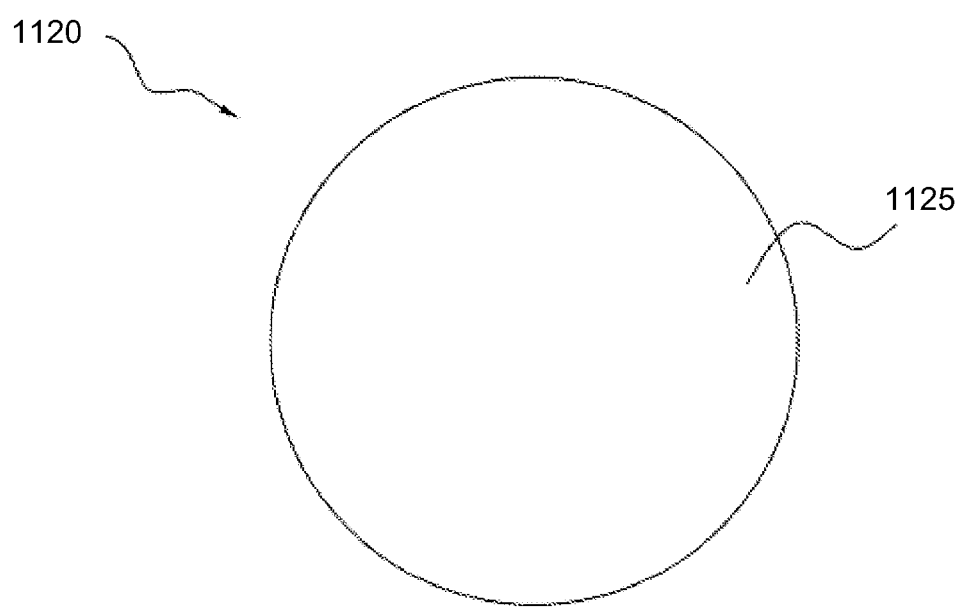
FIGS. 11-13 depict sets of exemplary membranes.
Figure 12:
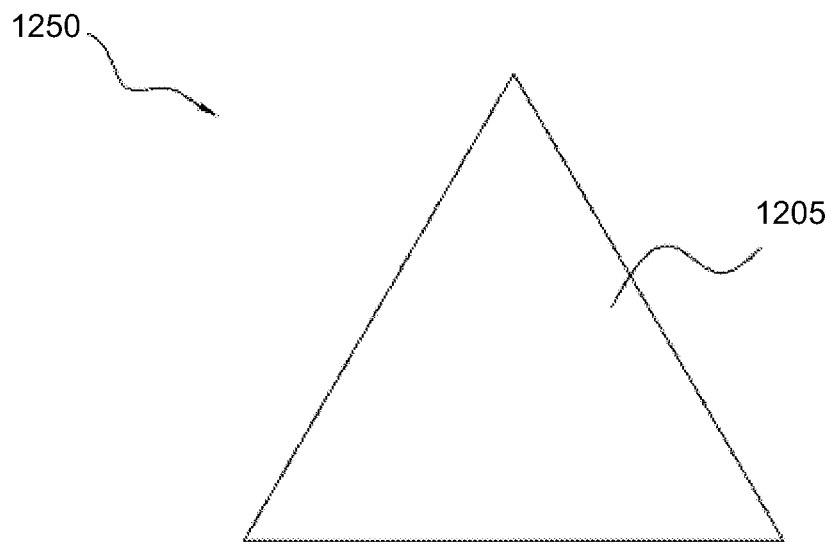
Figure 13:
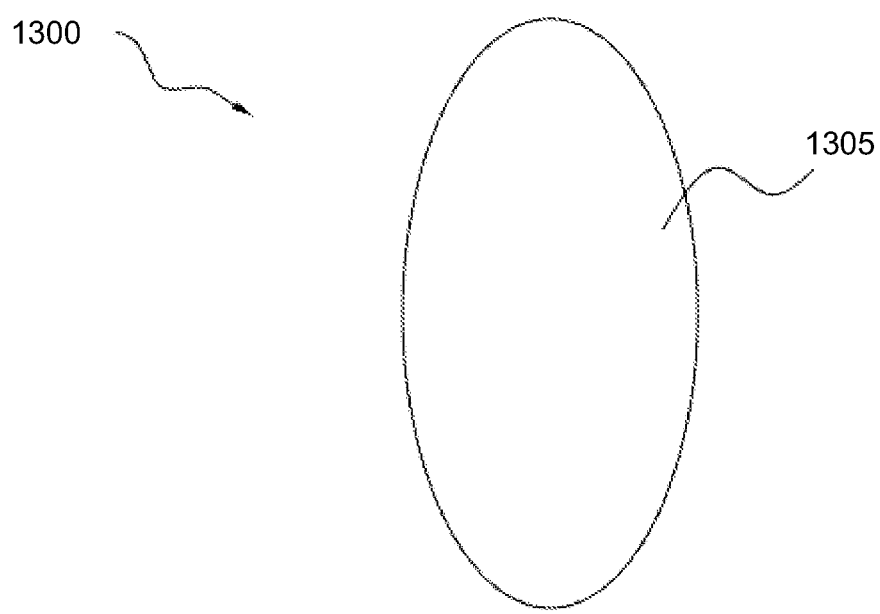

FIGS. 11-13 depict sets of exemplary shapes of the membrane described with reference, for example, to at least FIG. 8. The embodiments of FIGS. 11-13 may be implemented in a planar (flat) or on a support member with a curved surface (e.g., see membrane support member). It is speculated by the inventors that a curved surface may be advantageous in yielding a reduced tendency for the membrane to form to a patient's body contours, for example.

More particularly, FIG. 11 illustrates an exemplary embodiment 1120 including a membrane 1125 having a circular shape. FIG. 12 illustrates an exemplary embodiment 1250 including a membrane 1205 having a triangular shape. FIG. 13 illustrates an exemplary embodiment 1300 including a membrane 1305 having an elliptical shape.

Figure 14A:
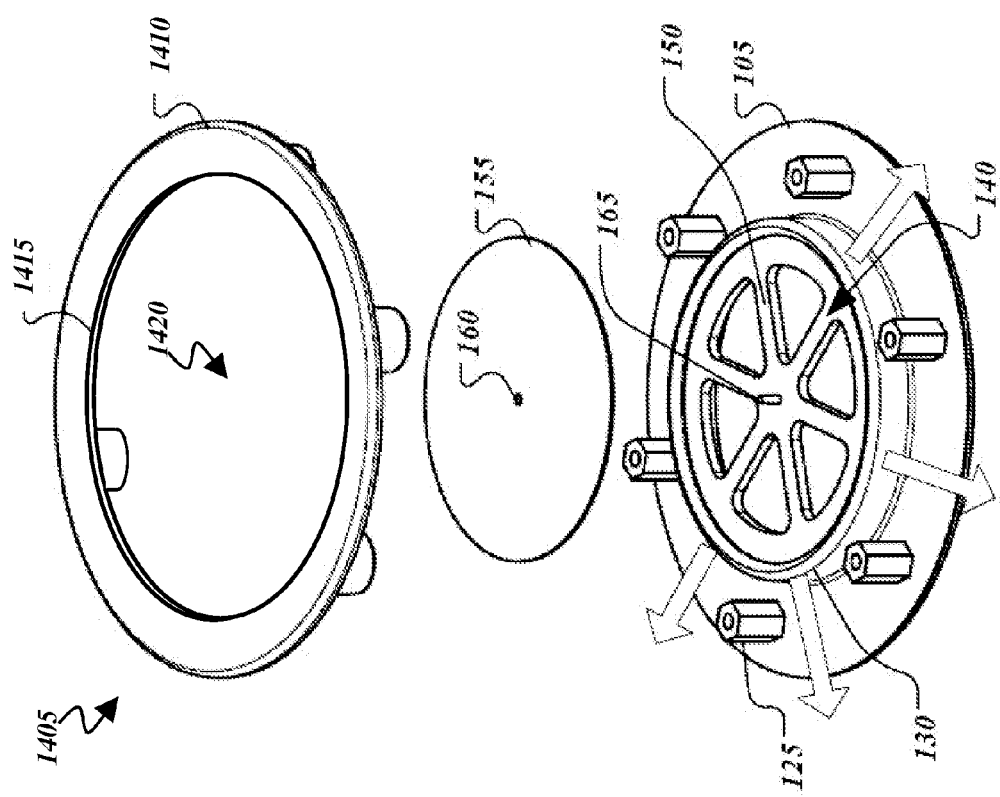

In the example depicted in FIG. 14A, a valve assembly 1405 includes the bottom housing 105, a top housing 1410 which is adapted to be coupled to the bottom housing 105, and the valve membrane 155 disposed between the top housing 1410 and the bottom housing 105. The top housing 1410 includes a central body portion and a plurality of radial protrusions 1415 extending from a periphery of the central body portion. In various implementations, the radial protrusions 1415 may advantageously substantially reduce or eliminate disruptions in the operation of the valve assembly 1405. For example, the radial protrusions 1415 may mitigate occlusion of adequate fluid communication through the valve assembly 1405 between the pleural cavity and ambient atmosphere, for example, due to blankets, clothing, bandages, bedding, and/or blood.

With reference to FIG. 1A, the radial protrusions 1415, in the depicted example, extend from a periphery of the lens 120. In this embodiment, no structural materials are present in the spaces between adjacent radial protrusions 1415. In an illustrative example, a compact radius embodiment may be particularly effective in dressing wounds in a field emergency situation, where the patient may be moved onto and off of gurneys and transported by helicopter and/or ambulance.

In some embodiments of the valve assembly 1405, the radial protrusions 1415 may extend radially outward starting from a greater distance from the center of the top housing 1410. For example, the radial protrusions 1415 may extend from a periphery of the top housing 110, an example of which is described at least with reference to FIG. 1A. In various implementations, occlusion mitigation at an increased radius from the center of the top housing 1410 may advantageously provide a larger annular volume 1535, an example of which is described at least with reference to FIG. 15A, through which may be more difficult to inadvertently occlude, for example, with blankets, clothing, bedding.

FIGS. 14A-14D depict exploded views of exemplary valve assemblies. FIG. 14A depicts an exemplary valve assembly 1405, which includes the bottom housing 105, a top housing 1410 which is adapted to be coupled to the bottom housing 105, and the valve membrane 155 disposed between the top housing 1410 and the bottom housing 105. The top housing 1410 includes a frame 1415 defining a central aperture 1420. With reference to FIG. 2A, in the depicted embodiment the valve system 140 of FIG. 2A is circumscribed within the central aperture 1420 when the assembly 1405 is assembled. In various implementations, the frame 1415 may advantageously substantially reduce or eliminate disruptions in the operation of the valve assembly 1405. For example, the frame 1415 may prevent occlusion of a valve assembly by bulk materials such as, for example, blankets, clothing, bandages, or bedding. In various implementations, circumscribing the valve system 140 within the central aperture 1420 may promote fluid communication from the pleural cavity through the valve system 140 in a perpendicular direction with respect to a plane tangent to the aperture 1420. In various implementations maintaining the valve system 140 inside the central aperture 1420 may allow the valve system 140 to be fully accessed. For example, the valve system 140 may be accessed to be rinsed via the central aperture 1420.

FIG. 14B depicts an exemplary valve top housing assembly 1425. The valve top housing assembly 1425 includes a top housing 1430 which may be used as an alternative for the top housing 1410 as depicted in FIG. 14A. With respect to FIG. 14A, the valve top housing assembly 1425 includes the top housing 1430 which is adapted to be coupled to the bottom housing 105 in FIG. 14A. The top housing 1430 includes a frame 1435 defining a central aperture 1420. With reference to FIG. 2A, the depicted valve system 140 of FIG. 2A is circumscribed within the central aperture 1420. Cross members 1440 are attached to the frame 1435 and span the central aperture 1420. In some implementations, the cross members 1440 may advantageously substantially reduce or eliminate disruptions in the operation of a valve assembly. For example, the cross members may substantially reduce or prevent occlusion of a valve assembly by bulk materials such as, for example, blankets, clothing, bandages, or bedding.

FIG. 14C depicts an exemplary valve top housing assembly 1445. The valve top housing assembly 1445 includes a top housing 1450 which may be used as an alternative for the top housing 1410 as depicted in FIG. 14A. With respect to FIG. 14A, the valve top housing assembly 1445 includes the top housing 1450 adapted to be coupled to the bottom housing 105 of FIG. 14A. The top housing 1450 includes the lens 120 and a plurality of radial protrusions 1455 extending from a periphery of the top housing 1450. With reference to FIG. 1A, the radial protrusions 1470, in the depicted example, extend from a periphery of the top housing 110. In this embodiment, no structural materials are present in the spaces between adjacent radial protrusions 1455. In various implementations, the radial protrusions 1470 may advantageously provide a larger annular volume 1535, which may be more difficult to inadvertently occlude, for example, with blankets, clothing, or bedding.

FIG. 14D depicts an exemplary valve top housing assembly 1460. The valve top housing assembly 1460 includes a top housing 1465 which may be used as an alternative for the top housing 1410 as depicted in FIG. 14A. With respect to FIG. 14A, the valve top housing assembly 1460 includes the top housing 1465 adapted to be coupled to the bottom housing 105 of FIG. 14A. The top housing 1465 includes a plurality of radial protrusions 1470 extending from a central portion of the top housing 1465. With reference to FIG. 1A, the radial protrusions 1470, in the depicted example, extend from a central portion of the top housing 110. With reference to FIG. 1A, the radial protrusions extend to a periphery of the top housing 110. In this embodiment, no structural materials are present in the spaces between adjacent radial protrusions 1470. In some embodiments, the radial protrusions 1470 aid fluid communication through the top housing 1465 by allowing fluid communication through the volume defined between the radial protrusions 1470.

With reference to FIG. 1A, the radial protrusions 1470, in the depicted example, extend from a central portion of the top housing 110. In some embodiments, the lens 120 may be omitted, leaving an opening in its place. In some embodiments, omission of the lens 120 may advantageously aid fluid communication in the vertical direction in addition to the lateral fluid communication from the pleural cavity through the valve assembly and through the volume defined between the radial protrusions 1470 to the ambient atmosphere. In various embodiments, one or more radial protrusions 1470 may be distributed around a portion or the entirety of the top housing 1465.

With reference to FIG. 1A, in some embodiments of the valve assembly 1460, the radial protrusions 1470 may extend beyond a radius corresponding to the periphery of the top housing 110. In various implementations, occlusion mitigation at an increased radius from the center of the top housing 1410 may advantageously provide a larger annular volume 1535, which may be more difficult to inadvertently occlude, for example, with blankets, clothing, or bedding.

FIGS. 15A-D depict cross sectional views of exemplary valve assemblies, such as those embodiments described with reference to FIGS. 14A-B. In FIG. 15A, a valve assembly 1505 includes a base 1510, a top housing 1520 adapted to be coupled to the base 1510, and one or more supports 1515 between the base 1510 and top housing 1520. The volume between the top housing 1520 and the base 1510 defines an annular cavity 1535 and a central cavity 1530. A valve 1525 is disposed inside the central cavity 1530. The valve 1525 is in fluid communication with the ambient atmosphere by a lateral path between the central cavity 1530, the annular cavity 1535, and around the one or more supports 1515. A plurality of radial protrusions 1540 are attached at a periphery of the top housing 1520. The radial protrusions extend beyond a periphery of the base 1510. The valve assembly 1505 is depicted as coupled to a carrier layer 1545.

In FIG. 15B, an exemplary valve assembly 1545 is depicted. The valve assembly 1545 includes a plurality of radial protrusions 1550 attached to a periphery of the top housing 1520. In some examples, the radial protrusions may be integrally formed and extend from the central top housing 1520. In some implementations, the radial protrusions may couple to the housing in a temporary or permanent manner.

By way of example and not limitation, the radial protrusions may clip on to the top housing, snap-in (e.g., tongue-in groove) fit, or threadingly engage the top housing 1520.

The radial protrusions 1550 extend downward. In some embodiments, the downward extension may substantially reduce or prevent the chance of occlusion of fluid flow through the valve assembly by excluding encroachment, for example, of bulk materials (e.g., fabric, clothing) into the annular cavity 1535 of the valve assembly.

In FIG. 15C, a valve assembly 1555 is depicted. The valve assembly includes a plurality of radial protrusions 1560 attached to the top housing 1520. In the depicted embodiment, the lateral dimension of the central body portion of the top housing 1520 is reduced such that the protrusions 1560 do not extend substantially beyond the lateral dimension of the base 1510. In the depicted embodiment, the annular cavity 1535 is formed in part by the volume defined between the base 1510 and the top housing 1520 and in part by the volume defined between the base 1510 and the radial protrusions 1560.

In FIG. 15D, an exemplary valve assembly 1565 includes a plurality of protrusions 1570 attached to or extending from the top housing 1520. In the depicted embodiment, the annular cavity 1535 is defined by the base 1510 and the radial protrusions 1570. In some embodiments, the radial protrusions 1570 defining the annular cavity 1535 may allow for increased fluid communication in a direction perpendicular to the radial protrusions 1570, for example, from the pleural cavity, through the valve 1525, and with reference to FIG. 14A, through the volume defined by the spacing between the radial protrusions 1415.

Figure 16A:
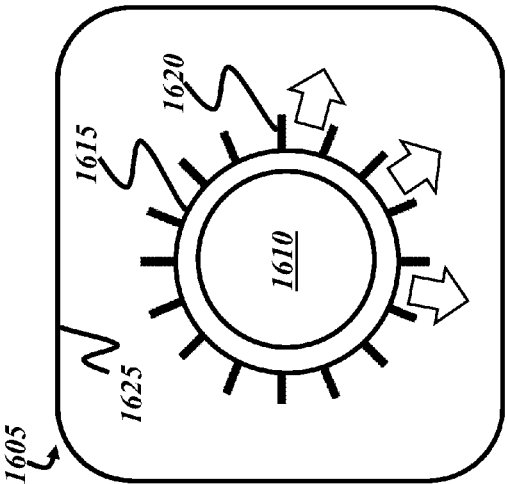
FIGS. 16A-D depict plan views of exemplary thoracic wound seal assemblies.

FIGS. 16A-D depict plan views of exemplary thoracic wound seal assemblies. In FIG. 16A, wound seal assembly 1605 includes a carrier layer 1625, a valve body 1610 coupled to the carrier layer 1625, and a plurality of radial protrusions 1620 coupled to the carrier layer 1625. The valve body 1610 includes a flange 1615. The plurality of radial protrusions 1620 extend radially and are operatively adjacent to a periphery of the flange 1615. Fluid communication through the wound seal assembly 1605 is radial from the center of the valve body 1610 through the periphery of the valve body 1610, through the flange 1615, and through the space defined between the radial protrusions 1620. In some embodiments, the radial protrusions 1620 may substantially reduce or prevent occlusion of lateral fluid communication at the periphery of the flange 1615.

Figure 16B:
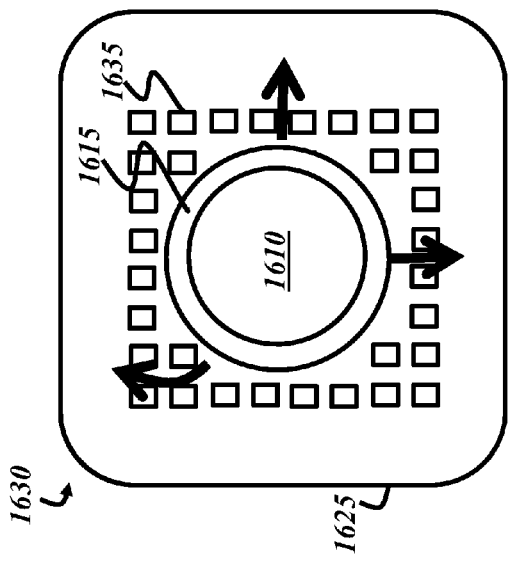

In FIG. 16B, an exemplary wound seal assembly 1630 includes the carrier layer 1625, the valve body 1610 coupled to the carrier layer 1625, and a plurality of bumps or nodules 1635 operatively adjacent to the valve body 1610 and coupled to the carrier layer 1625. The bumps or nodules 1635 define pathways that allow for lateral fluid communication between the periphery of the valve body 1610 and the ambient atmosphere. In the depicted embodiment, the bumps or nodules 1635 are rectangular. In some embodiments, the bumps or nodules 1635 may be square, triangular, circular, or combination of shapes suitable for maintaining fluid communication via lateral pathways between the nodules 1635. In some embodiments, the bumps or nodules 1635 may be attached to the carrier layer 1625 with an adhesive-backing, wherein the nodules 1635 may be slipped into position around the valve body 1610 and adhered to a top surface of the carrier layer 1625. In other embodiments, the bumps or nodules 1635 and carrier layer 1625 may form a unitary body.

In FIG. 16B, the bumps or nodules 1635 define pathways that allow for lateral fluid communication between the periphery of the valve body 1610 and the ambient atmosphere. In some examples, the bumps or nodules may allow the carrier layer 1625 and the wound seal assembly to be rolled or flexed in the area of the carrier layer 1625 containing the bumps or nodules 1635, for example, to more easily conform to the contours of a patient's body.

Figure 16D:
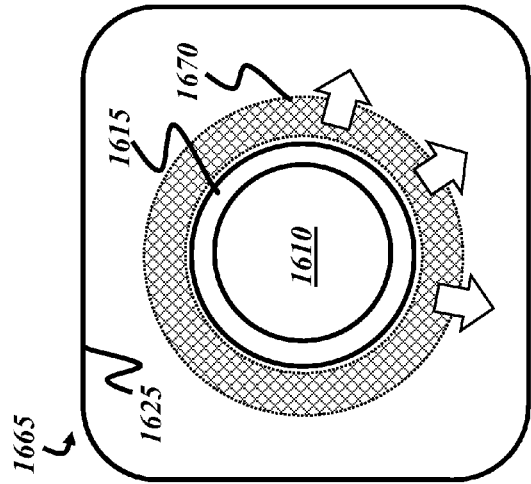
Figure 16C:
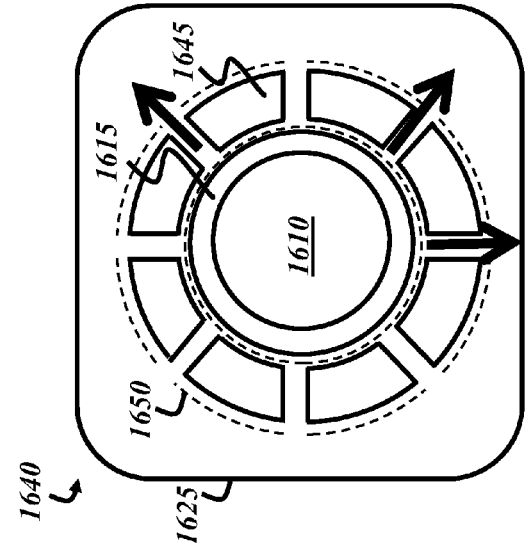

In FIG. 16C, an exemplary wound seal assembly 1640 includes the carrier layer 1625, the valve body 1610 coupled to the carrier layer 1625, and a plurality of structures 1645 operatively adjacent to the valve body 1610 and coupled to the carrier layer 1625. The structures are spaced from one another to form one or more pathways extending outward from the periphery of the valve body 1610. Fluid communication through the wound seal assembly may include radially and/or tangentially-directed components from the center of the valve body 1610, through the periphery of the valve body 1610, and through the pathways defined between the structures 1645.

In some embodiments, the structures 1645 and base layer 1650 may be attached to the carrier layer 1625 during manufacture. In some embodiments, the structures 1645 and base layer 1650 may be attached with an adhesive. In other embodiments, the structures 1645 and carrier layer 1625 may form a unitary piece of material, and base layer 1650 may be omitted. In other embodiments, the structures 1645 may be attached to the carrier layer 1625 during use. For example, one or more structures 1645 on a base layer 150 with a peel away adhesive backing could be included with a wound seal assembly as part of a kit. With reference to at least FIGS. 16A and 16B, the described methods of attachment may also apply to the radial protrusions 1615 and bumps or nodules 1635.

In FIG. 16D, an exemplary wound seal assembly 1665 includes the valve body 1610, with an open cell foam or mesh ring 1670 operatively adjacent to the valve body 1610. The valve body 1610 and open cell foam or mesh ring 1670 are coupled to a carrier layer 1625. In some embodiments, the open cell foam or mesh ring 1670 may allow for lateral fluid communication from the periphery of the valve body 1610 through the material comprising the open cell foam or mesh ring 1670. In some embodiments, the open cell foam or mesh ring 1670 may reduce or prevent occlusion of the valve body 1610 by bulk materials during use. In some embodiments, the open cell foam or mesh ring 1670 may function as a particulate filter. By way of example but not limitation, the open foam cell or mesh ring 1670 may include a thin screen covering lateral apertures in the valve body 1610.

FIG. 17A-C depict cross sectional views of exemplary thoracic wound seal assemblies, examples of which are described with reference to FIG. 16.

In FIG. 17A, an exemplary wound seal assembly 1705 includes a valve housing 1710 defining an annular cavity 1725 and a central cavity 1720. A valve 1715 is disposed inside the central cavity 1720. A plurality of structures 1730 are operatively adjacent the valve housing 1710. The structures 1730 and the valve housing 1710 are coupled to a carrier layer 1755. The valve 1715 is in fluid communication with the ambient atmosphere by a lateral path between the central cavity 1720, the annular cavity 1725, and pathways defined between the plurality of structures 1730. With reference to FIGS. 16A-D, the pathways between the structures 1730 correspond to pathways defined by the spacings between radial protrusions 1620, by the spacings between bumps or nodules 1635, by the spacings between the structures 1645, or through the material comprising the foam or mesh ring 1670.

In FIG. 17B, an exemplary wound seal assembly 1735 includes a plurality of structures 1740 spaced at a distance from the valve housing 1710. The structures 1740 and the valve housing 1710 are coupled to a carrier layer 1755. In some examples, the spacing between the structures 1740 and the valve housing 1710 allows the carrier 1755 layer to flex to conform to a user's body. With reference to FIGS. 16A-D, the spacing between the structures 1740 and the valve housing 1710 may correspond, in some embodiments, to spacing defined between the valve body 1610 and the radial protrusions 1620, the bumps or nodules 1635, the structures 1645, or the foam or the mesh ring 1670.

In FIG. 17C, a valve assembly 1745 includes a plurality of structures 1750 operatively adjacent the valve housing 1710. The structures 1750 and the valve housing 1710 are coupled to a carrier layer 1755. The spacing between structures 1750 define pathways which allow for lateral air flow away from the valve housing 1710. With reference to FIGS. 16A-D, the pathways between the structures 1750 correspond to pathways defined by the spacings between radial protrusions 1620, by the spacings between the bumps or nodules 1635, by the spacings between the structures 1645, or through the material that forms the foam or mesh ring 1670. In the valve assembly 1745, the valve housing 1710 has a central cavity 1720 and a minimal or no overhanging feature. For example, with reference to FIGS. 16A-D, the valve housing 1710 corresponds to the valve housing 1610 with no flange 1615. In some examples, removing or reducing the flange that forms the annular cavity from the valve housing allows for a reduced-diameter, more compact valve housing 1710. In some examples, a smaller valve housing 1710 may allow a wound seal assembly to be more easily rolled for compact storage (e.g., in a medical pouch). In various examples, a smaller valve housing may allow a wound seal assembly to more readily conform to the contours or motion of a user's body.

FIG. 18A-B depicts cross sectional views of exemplary thoracic wound seal assemblies. In FIG. 18A, an exemplary wound seal assembly 1805 includes a bottom housing 1825 coupled to one or more supports 1860, coupled to a top housing 1810. The volume between the top housing 1810 and bottom housing 1825 defining a central cavity 1820. A valve 1815 is disposed inside the central cavity 1820. The valve housing is coupled to a carrier layer 1855. The valve 1815 is in fluid communication with the ambient atmosphere by one or more lateral pathways between supports 1860. In some embodiments, the top housing may reduce or prevent the chances for occlusion of fluid communication through the wound assembly during use, such as, for example, occlusion or interference with the valve 1815 by bulk materials.

In FIG. 18B, wound seal assembly 1805 includes a bottom housing 1825 coupled to one or more supports 1860, coupled to a top housing 1810. The volume between the top housing 1810 and bottom housing 1825 defining a central cavity 1820. A valve 1815 is disposed inside the central cavity 1820. The valve housing is coupled to a carrier layer 1855. The valve 1815 is in fluid communication with the ambient atmosphere by one or more lateral pathways between supports 1860. An open cell foam or mesh 1870 is disposed at a periphery of the central cavity 1820. In some embodiments, the open cell foam or mesh 1870 may function as a particulate filter. In some embodiments, for example, the open cell foam or mesh 1870 may comprise a thin screen.

Figure 19A:
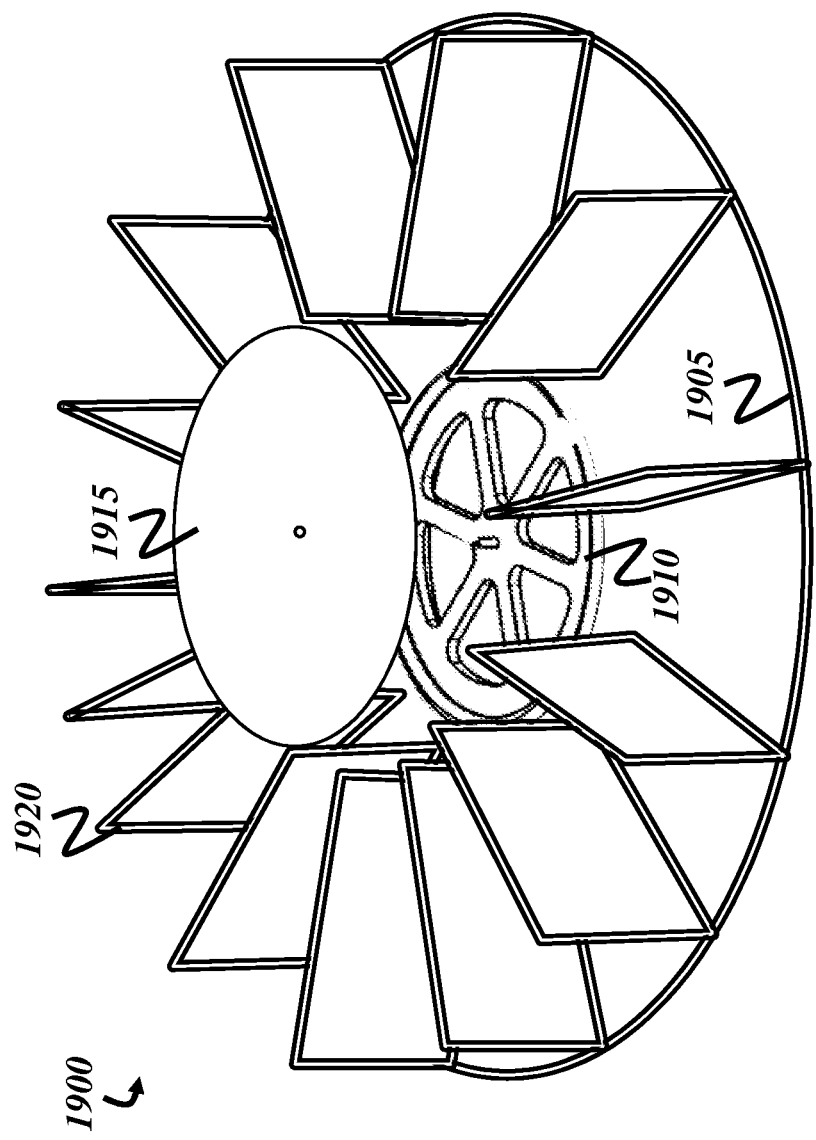
FIGS. 19A-B depict exploded views of exemplary valve assemblies.
Figure 19B:
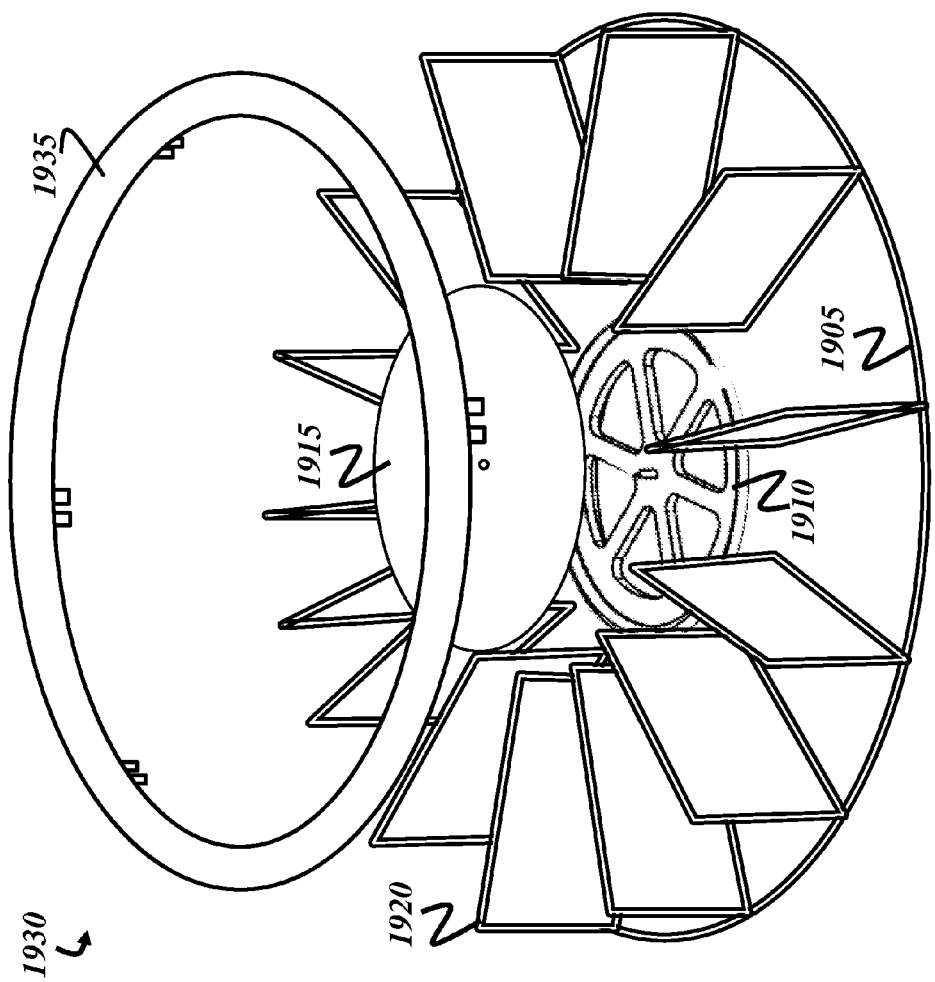

FIGS. 19A-B depict exploded views of exemplary valve assemblies. In FIG. 19A, an exemplary valve assembly 1900 includes a base 1905, a valve 1910 coupled to the base 1905, and a valve membrane 1915 disposed on the valve 1910. A plurality of structures 1920 are disposed around the periphery of the valve 1910 and coupled to the base 1905. The structures 1920 define pathways for fluid communication between a periphery of the valve 1920 and the ambient atmosphere. In some embodiments, the structures 1920 prevent or greatly reduce the possibility of the occlusion of fluid communication through the valve due to bulk materials which can block the valve.

In FIG. 19B, an exemplary valve assembly 1930 includes the base 1905, the valve 1910 coupled to the base 1905, and the valve membrane 1915 disposed on the valve 1910. The plurality of structures 1920 are disposed around the periphery of the valve 1910 and coupled to the base 1905. Protective members 1935 are disposed to overlie the valve 1910. In some embodiments, the protective members 1935 prevent or greatly reduce the possibility of the occlusion of fluid communication through the valve due to bulk materials which can block the valve.

Although various embodiments have been described with reference to the figures, other embodiments are possible. For example, portions of the housings 105, 110 may be coated with active materials, such as anti-microbials (e.g., silver). Some portions of the valve, such as the valve membrane and/or the interior surfaces of the valve housing may be partially or completed coated with a lubricious material to promote the flow of exudates, which may reduce the risk of occlusion of valve pathways.

Some embodiments of the valve assembly may omit the lens. In some applications, this may permit use of stronger, thinner plastic materials. In some examples, omission of the lens may permit a lower profile, which may be more comfortable when the patient lies down on the side with the valve assembly. Lower profiles may also permit the valve cavity to be enlarged to accommodate larger wounds.

In some implementations, it may be advantageous to provide a bandage or wound seal without the valve assembly. For example a wound seal may be formed of a carrier, a hydrogel, and an anti-microbial agent included in the hydrogel. The hydrogel may be stored between the carrier and a release liner that can be rapidly removed when needed for use as a wound dressing.

In various embodiments, the membrane may have visual indicia to make it easier to detect operation of the membrane that may be associated with pressure release from the thoracic cavity. In some examples, the membrane itself may be tinted yellow to distinguish it from the other substances that may be present in the valve (e.g., blood). The membrane may have dots, stripes, or other variations in color or makings to help the observer readily distinguish and identify the membrane through the lens, and to verify correct operation of the valve membrane, for example.

In some embodiments, such as those described with reference to FIGS. 3A-3B, means for attaching the carrier 300 to the base 305 include a compressive interference between the valve flange 390 and the base flange 310. In another embodiment, the valve flange 390 may be configured with a number of plastic posts that penetrate the carrier 330; in assembly, the posts may be transformed (e.g., by ultrasonic welding or heat staking process) into a shape or form (e.g., rivet head) that retains the carrier 330.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A thoracic valve seal system, comprising:
   a carrier layer formed of a substantially pliable sheet material;
   an adhesive material on one surface of the carrier layer;
   a valve that permits fluid to flow through the valve in substantially only one direction, the valve having a flexible membrane;
   a housing that couples to the carrier layer and that, when sealed around a wound by the adhesive material on the carrier layer, supports the valve in an orientation relative to the patient's body to permit fluids to flow substantially only from the wound to a region outside of the body, the housing comprising:
   a bottom housing that includes a sealing cavity to provide fluid communication from the wound to the valve when sealed around the wound;
   a top housing that couples to the bottom housing, wherein the top housing includes a flange that extends radially around a periphery of the valve to form an annular space between the top housing and the bottom housing; and,
   a lens to magnify an image of the valve.

2. The thoracic valve seal system of claim 1, wherein the adhesive material comprises a hydrogel.

3. The thoracic valve seal system of claim 1, wherein the adhesive material further comprises an ingredient with an effective amount of an anti-microbial agent.

4. The thoracic valve seal system of claim 1, further providing an annular coupling from the housing to a periphery of the flexible membrane.

5. The thoracic valve seal system of claim 1, wherein the top housing and the bottom housing include a plurality of interference fit features to mate to each other.

6. The thoracic valve seal system of claim 1, wherein the top housing and the bottom housing include a plurality of interference fit features extending between the top and the bottom housing to mate to each other and to couple the housing to the carrier layer.

7. The thoracic valve seal system of claim 1, wherein the provided housing forms an aperture that provides fluid communication from an exhaust side of the valve to the annular space between the top housing and the bottom housing.

8. The thoracic valve seal system of claim 1, wherein the valve membrane may be color-tinted to substantially contrast with typical exudes.

9. The thoracic valve seal system of claim 8, further comprising a cavity to provide fluid communication through the apertures in a plane substantially parallel to a plane tangent to the wound.

* * * * *